United States Patent
Welter et al.

(10) Patent No.: US 12,349,676 B2
(45) Date of Patent: Jul. 8, 2025

(54) PARTICLES WITH BIOCIDAL COATING

(71) Applicant: instrAction GmbH, Heidelberg (DE)

(72) Inventors: Martin Welter, Neckargemünd (DE); Christian Meyer, Schwetzingen (DE); Kristian Lungfiel, Wiesbaden (DE)

(73) Assignee: instrAction GmbH, Heidelberg (DE)

( * ) Notice: Subject to any disclaimer, the term of this patent is extended or adjusted under 35 U.S.C. 154(b) by 857 days.

(21) Appl. No.: 17/437,279

(22) PCT Filed: Mar. 13, 2020

(86) PCT No.: PCT/EP2020/056866
§ 371 (c)(1),
(2) Date: Sep. 8, 2021

(87) PCT Pub. No.: WO2020/187746
PCT Pub. Date: Sep. 24, 2020

(65) Prior Publication Data
US 2022/0159949 A1    May 26, 2022

(30) Foreign Application Priority Data

Mar. 15, 2019 (DE) .................. 10 2019 106 646.8

(51) Int. Cl.
| | | |
|---|---|---|
| *A01N 25/26* | (2006.01) | |
| *A61L 2/232* | (2006.01) | |
| *B01J 39/02* | (2006.01) | |
| *B01J 39/09* | (2017.01) | |
| *B01J 39/12* | (2006.01) | |
| *B01J 41/05* | (2017.01) | |
| *B01J 41/07* | (2017.01) | |
| *B01J 41/14* | (2006.01) | |
| *C02F 1/42* | (2023.01) | |
| *C02F 1/50* | (2023.01) | |
| *A61L 101/46* | (2006.01) | |
| *C02F 101/20* | (2006.01) | |

(52) U.S. Cl.
CPC .............. *A01N 25/26* (2013.01); *A61L 2/232* (2013.01); *B01J 39/02* (2013.01); *B01J 39/09* (2017.01); *B01J 39/12* (2013.01); *B01J 41/05* (2017.01); *B01J 41/07* (2017.01); *B01J 41/14* (2013.01); *C02F 1/42* (2013.01); *C02F 1/50* (2013.01); *A61L 2101/46* (2020.08); *C02F 2001/422* (2013.01); *C02F 2101/20* (2013.01); *C02F 2303/04* (2013.01)

(58) Field of Classification Search
CPC ........ A01N 25/26; A01N 25/10; A01N 33/04; A61L 2/232; A61L 2101/46; B01J 39/02; B01J 39/09; B01J 39/12; B01J 41/05; B01J 41/07; B01J 41/14; B01J 20/3204; B01J 20/321; B01J 20/3272; B01J 20/3282; B01J 20/3293; B01J 47/016; C02F 1/42; C02F 1/50; C02F 2001/422; C02F 2101/20; C02F 2303/04; C02F 1/285; C02F 2101/103; C02F 1/288; B01D 2239/0442; B01D 2239/0485; B01D 39/06; C09D 5/14

See application file for complete search history.

(56) References Cited

U.S. PATENT DOCUMENTS

| | | | |
|---|---|---|---|
| 11,014,071 | B1 | 5/2021 | Welter et al. |
| 11,633,718 | B2 * | 4/2023 | Welter ................... A01N 61/00 |
| | | | 210/502.1 |
| 2005/0263453 | A1 | 12/2005 | Collias et al. |
| 2017/0304804 | A1 * | 10/2017 | Kim ...................... B01J 27/1806 |
| 2020/0171463 | A1 | 6/2020 | Meyer et al. |
| 2020/0197908 | A1 * | 6/2020 | Welter ................... A01N 61/00 |

FOREIGN PATENT DOCUMENTS

| | | | | |
|---|---|---|---|---|
| CA | 2734310 | A1 * | 9/2011 | ............. C02F 1/285 |
| DE | 102017007273 | A1 | 2/2019 | |
| EP | 2570182 | A1 | 3/2013 | |
| JP | 2010254841 | A | 11/2010 | |
| WO | 2016030021 | A1 | 3/2016 | |
| WO | 2017089523 | A1 | 6/2017 | |
| WO | WO-2019025488 | A1 * | 2/2019 | ............. A01N 25/34 |

OTHER PUBLICATIONS

International Search Report and Written Opinion for International Application No. PCT/EP2016/056866, dated Jun. 19, 2020, 7 pages.
"Status Report on ADONA and perfluorinated substances", Dec. 2016, 15 pages, Bavarian State Office for Health and Food Safety.
"Point of Use Water Treatment Systems Market", Oct. 2017, 8 pages, Grand View Research, Inc.

* cited by examiner

*Primary Examiner* — Sean M Basquill
(74) *Attorney, Agent, or Firm* — Matney Legal Group PLLC

(57) ABSTRACT

Process for the preparation of particles with antibacterial coating, which comprises the following steps: (a) providing an aqueous suspension containing a polyamine, a crosslinker and a porous organic or inorganic carrier material in particle form at a temperature lower than or equal to 10° C. in a mixer for coating the inorganic carrier material with the polyamine; (b) crosslinking the organic polymer in the pores of the inorganic carrier material and simultaneously removing water.

12 Claims, 4 Drawing Sheets

PARTICLES WITH BIOCIDAL COATING

CROSS REFERENCE TO RELATED APPLICATIONS

This application is a U.S. National Phase Patent Application of International Application No. PCT/EP2020/056866, filed Mar. 13, 2020, which claims priority to Germany Patent Application No. DE 10 2019 106 646.8, filed Mar. 15, 2019, the disclosures of which are herein incorporated by reference in their entireties for all purposes.

FIELD OF THE INVENTION

The present invention relates to the preparation of absorber resins for the removal of heavy metals, anions of elementic or elementous acids as well as specific micropollutants and bacteria from aqueous solution, wherein one process comprises the purely external coating of commercial ion exchangers or the complete coating of porous polymer particles with an amino-group-containing polymer and the subsequent modification of the polymer with functionalizing ligands.

BACKGROUND OF THE INVENTION

According to reports from the World Economic Forum (2015), the water crisis is defined as the number one global risk that will affect the entire global population.

The World Health Organization (WHO) and UNICEF also highlight that 663 million people in the world currently do not have access to clean drinking water and 2.4 billion people use water sources of inadequate quality (as at 2015).

The overall situation has several causes, wherein mention may be made here of continuous population growth, a reduction in water sources due to climate change and global warming as well as increasing pollution of water sources contaminated by industrial waste. It is therefore of decisive importance to increase the quality of drinking water and to reduce water pollution.

Sources of drinking water can be contaminated by various pollutants. These include chemicals, bacteria, micropollutants and heavy metals. These contaminants must be removed from the water before drinking, for health reasons.

There are several possible ways of removing contaminants in order to obtain safe and clean drinking water. The most widespread technique is mechanical filtration, which is achieved using different techniques and processes. It is imperative that contaminants are filtered with the aid of a filter, a membrane or the like with a defined pore size which is smaller than the contaminant.

Reverse osmosis is one of these filtration methods, in which the majority of the water to be filtered is discarded as waste (approx. 90%), with high operating costs (e.g. electricity requirement). In view of the exhaustion of water sources in the world today, it is important to develop cost-efficient and water-saving technologies for drinking water filtration.

It is now apparent that none of the technologies available on the market alone can cover all areas of the possible spectrum of contaminants. This also applies to the resins supplied by instrAction GmbH, which for example cannot remove "chlorine" from water. As a result, there is demand for an intelligent and novel combination of known purification technologies (for example activated charcoal for "chlorine") with innovative absorber resins for the removal of heavy metals, anions of elementic acids or elementous acids, micropollutants and bacteria.

The productivity is, with a given contaminant profile and desired depletion rates, substantially determined by the necessary residence time in the absorber resin bed. For example, small particles are to be preferred here because of the short diffusion paths for the contaminants, which on the other hand increase the counterpressure in an undesired manner, however. Larger particles may require a larger bed, as small beds can be stably packed with large particles only with difficulty; on the other hand, they very probably require a longer residence time because of the longer diffusion paths.

With respect to the competing technologies available on the market, reverse osmosis (RO) is the most widely used technique. According to the 2017 market study by Grand View Research (Market Research Reports & Consulting), it has a market share of approx. 44% in the field of domestic drinking water treatment. In total, approx. 210 million units were sold worldwide in 2016.

A serious disadvantage of RO modules is their very poor yield. Only approx. 10-20% of the water introduced is actually purified and available to the customer. A further disadvantage is the necessity to use electricity for a required pump and the quality of the water: RO systems supply pure water without essential salts, which must then be added again (e.g. calcium and magnesium).

The disadvantage of extremely high energy consumption is common to distillation processes. Moreover, there, as in the case of reverse osmosis, the health-promoting elements are also removed, with the result that distilled water forms which is not suitable for long-term consumption, and important ingredients such as magnesium salts must again be added in a subsequent step.

The water purification machines which combine several filtering techniques in separate units/cartridges require complex piping with corresponding valves or connectors, which are however susceptible to faults and open up the possibility of leaks, etc. Moreover, connections are precisely the points at which bacteria, etc. have particularly good opportunities to grow because of the flow conditions.

A known filter medium utilized on the market is e.g. activated charcoal, which is used as a packed bed of particles in cartridges with linear throughflow or as a pressed hollow cylinder with radial throughflow.

The ion exchanger resins, which likewise bind heavy metals, do this in competition with calcium and magnesium and are thus unreliable, or the heavy metals are rinsed out of the resin in a small volume in concentrated form, shortly before the total capacity of the ion exchanger is exhausted. At the same time, the status of exhaustion is reached very quickly in particular when hard water is present. From this point in time, heavy metals are no longer removed either. Rather, the heavy metal ions already immobilized on the ion exchanger are eluted in a comparatively small volume because they are displaced by the excess of alkaline earth metals present. At the same time, sodium ions are released into the water by the ion exchanger: a high sodium content in drinking water is regarded increasingly sceptically in connection with baby food and cardiovascular diseases. In addition to the heavy metals, anions of elementic acids and elementous acids, such as selenides, selenates, arsenides and arsenates, are to be regarded with scepticism with regard to the health of consumers and water consumers.

The object resulting from this is to prepare stable and inexpensive absorber materials for heavy metals and anions of elementic acids and elementous acids, which purify water reliably and with a high yield and at the same time still remove bacteria.

SUMMARY OF THE INVENTION

The object is achieved by a process for the preparation of particles with antibacterial coating, wherein the process comprises the following steps:
(a) providing an aqueous suspension containing a polyamine, a crosslinker and a porous organic or inorganic carrier material in particle form at a temperature lower than or equal to 10° C. in a mixer for coating the inorganic carrier material with the polyamine;
(b) crosslinking the organic polymer in the pores of the inorganic carrier material and simultaneously removing water.

Within the meaning of the invention it is preferred for steps a) and b) to be repeated at least once.

According to a preferred embodiment of the process, the crosslinking is effected in a stirred reactor.

It has proved advantageous for the polyamine to be used in the non-desalinated state.

The organic carrier polymer is preferably a polystyrene.

According to a further embodiment, the organic carrier polymer is a strong or a weak anion exchanger, which is coated with the polymer only on its outer surface. Those organic polymers which have sulfonic acid groups are called strong anion exchangers. Weak anion exchangers are polymers which have carboxylic acid groups.

According to a further embodiment of the invention, the organic polymer is selected from polystyrene, polymethacrylate and polyacrylate.

The polymer can also be an inorganic polymer, selected from silica gel and hydroxyapatite.

In addition, it is preferred if the polyamine is a polyvinylamine.

A further subject of the invention is biocidal, porous particles, preferably of a crosslinked polyamine, which can be obtained or are prepared according to the process described above.

A still further subject of the invention is heavy-metal-absorbing porous particles which are prepared according to the process described above.

A further subject of the invention is absorbing porous particles, which absorb the anions of elementic or elementous acids such as selenite, selenate, arsenite and arsenate, wherein the particles can be obtained or are prepared according to the process described above.

DETAILED DESCRIPTION OF THE INVENTION

The compounds from groups 15 and 16 (previously main groups 5 and 6) of the Periodic Table which bear four oxygen atoms are called elementic acids or anions of elementic acids, thus e.g. $H_3AsO_4$ or $AsO_4^{3-}$, $H_3SeO_4$ or $SeO_4^{3-}$.

The compounds from groups 15 and 16 of the Periodic Table which bear three oxygen atoms are called elementous acids or the anions of elementous acids, thus e.g. $H_3AsO_3$ or $AsO_3^{3-}$, $H_3SeO_3$ or $SeO_3^{3-}$.

Like activated charcoal, ion exchangers also suffer from microbial contamination and biofilm formation on their surface. Thus, in the end, they see to it that even drinking water of low microbial contamination contains more bacteria after the so-called "purification" than before it.

The object resulting from this is to provide ion exchangers, such as are used in the softening of drinking water, with an antibacterial surface, without appreciably reducing the capacity of the ion exchangers.

At the same time potentially toxic micropollutants are increasingly becoming a focus of public interest and experts.

This applies in particular to perfluorinated surfactants (e.g. perfluorooctanoic acid, perfluorooctanesulfonic acid), which are not or are hardly biodegradable and therefore have a very high persistence ("Sachstandsbericht ADONA and perfluorierte Substanzen" ["Assessment report ADONA and perfluorinated substances"], source: Bavarian State Office for Health and Food Safety).

A range of very inefficient and expensive methods exist for the removal of perfluorinated surfactants from drinking water, such as for instance filtration through activated charcoal, which has only a very low capacity for this type of contaminant, or membrane processes, which, although they provide clean drinking water, at the same time produce large quantities of waste water which contain the perfluorinated surfactants in concentrated form. Moreover, they must be disposed of (as a rule incinerated) at a cost, or they enter the waste water again. To our knowledge there is currently no selective absorber with high capacity for perfluorinated surfactants.

The object resulting from this is to modify and further develop known resins in such a way that in addition to the heavy metals and bacteria they also remove perfluorinated surfactants from drinking water.

It is known of resins that they can remove heavy metals (WO2015EP01754, WO2016EP78787) and bacteria (DE102017007273.6) from drinking water. Here an amino polymer is immobilized on corresponding carriers, reacted with a bifunctional crosslinker to form a stable three-dimensional network. The resins are therefore suitable both as filters for heavy metals in drinking water purification plants and for "police filters" for the removal of heavy metals at the end of a purification cascade of orthogonal methods.

In the first step of the resin preparation, the required coating polymer, polyvinyl formamide, is produced and hydrolyzed by means of sodium hydroxide solution in a polymer-analogous reaction to form polyvinylamine (PVAm). Then the reagents and separation products are removed by a time-consuming and cost-intensive crossflow filtration. This desalinated polymer solution is now used in the second step for coating the carrier material.

The object resulting from environmental issues (reduction of energy consumption and the quantities of waste water) and the market requirements for drinking water purification systems is to simplify the preparation processes, and make them cheaper and more resource-conserving.

Up to now it was known only that the so-called MetCap® particles can successfully remove bacteria from solutions (DE102017007273.6) which either are based on silica gel or manage without carriers. Preparation and detection of the activity are disclosed in DE102017007273.6. There the coating of silica gel particles (as template) with non-desalinated polymer and subsequent dissolution of the inorganic carrier and its antibacterial activity are described.

For particles which are based on an organic carrier, for example polystyrene, no corresponding activity was known up to now. This activity could now surprisingly be established on the polystyrene-based resin prepared according to the new process. This observation is surprising because polystyrenes usually tend towards pronounced biofilm formation and certainly do not remove bacteria. Evidently the novel coating ensures that the bacteria do not grow on the polystyrene surfaces, but rather are bound out of the matrix, here drinking water.

A range of objects resulting for the named reasons is to develop and further develop the known resins, with the following aims:

simplification of the current preparation process for producing the instrAction MetCap and BacCap resins, reduction of the waste stream, the expansion of the product range through a combination of ion exchanger properties of softening with the already known properties of metal- or bacteria-binding as well as the preparation of absorber resins for binding perfluorinated surfactants, which represent a growing problem in drinking water treatment.

Furthermore, an expansion of the product range to organic carriers, for example polystyrene, would be of great advantage because they can be obtained inexpensively in different specifications with respect to particle size and pore size. Polystyrenes have good mechanical properties for the application and are well established on the market.

The simplification of the preparation process using polystyrene-based resins is achieved by dispensing with the desalination of the polymer hydrolysate as well as by further process changes, which relate in particular to the addition and drying of the carrier polymers to form the polymer solution.

Surprisingly, it is possible to prepare MetCap® and BacCap® resins without prior desalination of the polymer solution by immobilization on porous polystyrene particles. This is all the more surprising as, in earlier studies, the deposition or immobilization rate of the polymer on the porous carrier was found to be clearly dependent on the salt content of the polymer hydrolysate.

Through adjustments in the coating process (e.g. multiple coating, drying in a Lödige ploughshare mixer, introduction of new washing strategies), the complex and costly process step of desalination of the polymer hydrolysate could be dispensed with, without having to accept limitations in the efficiency of the products.

In summary, it can be said that changing the preparation process, in particular dispensing with the desalination through membrane filtration, and expanding to organic carrier materials bring decisive advantages.

The polymer content is now determined by the batch calculation during the polymerization. The coating and pre-crosslinking with ethylene glycol diglycidyl ether in a Lödige vacuum shovel dryer functions exactly the same as with the PVAm polymer solution which contains no salts, to the surprise of the authors. The contained salts are then partially dissolved out during the preparation of the suspension for the post-crosslinking. After the silica gel of the carrier has been brought into solution with the aid of the sodium hydroxide solution, all salts (silicates, formates, chlorides, etc.) are rinsed out of the crosslinked, purely organic template material. The thus-obtained BacCap® T or MetCap® T material has the same properties as the absorber resins which were prepared according to the process with the desalinated PVA polymer. This is the first improvement in the process, which comes as a big surprise because the prevailing assumption to date, which was also proven by data in the literature, is that the volume requirement of the highly concentrated salts in the polymer solution would prevent an effective and complete filling of the particles with polymer, solely due to its dimensions.

The second process relates to the coating of commercial strong or weak ion exchangers with an antibacterial PVA polymer shell.

Commercial ion exchangers, specifically the cation exchangers used here, as a rule have acid groups which are covalently bound to the polymeric carrier (e.g. polystyrene, acrylates etc.). The acid groups are carboxylic acids or carboxylates in the case of weak ion exchangers or sulfonic acids or sulfonates in the case of strong ion exchangers. Both types are used in the softening of drinking water.

In order to provide these ion exchangers with antibacterial properties and at the same time not to significantly reduce their softening capacity, only an external coating of the particles is sought, without modifying the acid groups in the pores of the particles, where the majority of the capacity-carrying acid groups are located.

This aim is achieved by using a corresponding polymer which cannot penetrate into the pores of the ion exchanger particles because of its size and its hydrodynamic radius. The pore sizes in the case of commercial ion exchangers lie in the range of from 20 nm to 100 nm. For polymers with a size of 10,000-20,000 g/mol these pores are impenetrable.

In this procedure, in a preferred embodiment, only the outer 2-25% of the particle, measured at the radius of the particle, is coated. More preferably, only the outer 2-10% of the particle, measured at the radius of the particle, is coated. Most preferably, only the outer 2-5% of the particle, measured at the radius, is coated.

By far the majority of the groups capable of ion exchange remains available in this way for the softening of the water.

The non-desalinated polymer of corresponding size can also be used for this, but it does not represent a compulsory prerequisite. The coating with desalinated polymer is also possible, as is the use of non-desalinated polymer.

After the hydrolysis of the amide groups of the polyvinylamine with sodium hydroxide solution and the subsequent neutralization with hydrochloric acid, the polymer contains approx. 15-25 wt.-% salt in the form of sodium formate and sodium chloride. The polymer content of the aqueous solution corresponds to 9-13 wt.-% in the case of the non-desalinated polymer.

In the processes to date, the salts were removed in a complex manner by reverse osmosis, and the polymer with a salt content of less than 2.5 wt.-% was used. The new process allows this complex and expensive desalination step to be dispensed with. It is therefore preferred, with the new process, to use the polymer partially desalinated with a salt content of 2.5-15 wt.-%. It is more preferred to use a partially desalinated polymer with a salt content of 10-15 wt.-%. It is most preferred to use a non-desalinated polymer with a salt content of 15-25 wt.-%.

EXAMPLES

Example 1

1712 g moist carrier material, Lewatit S1567 ion exchanger, is conveyed directly into a VT5 ploughshare mixer from Lödige. The ion exchanger is then dried for 60 min at 80° C. The moisture loss is determined by weighing the dried ion exchanger. 380 g water has been removed. The product temperature in the dryer is adjusted to 10° C. The mixer is operated at 180 revolutions per minute. Once the product temperature in the mixing drum has reached 10° C., 225 g of the ion exchanger, non-desalinated polyvinylamine solution batch: PC 18007 (polymer content 10%) cooled to 10° C., and 1 g ethylene glycol diglycidyl ether (EGDGE)

[2224-15-9] are weighed out into a vessel and deionized water is added until a total volume of 350 ml has been reached. The mixture is placed in the mixer within 10 min and mixed for 1 h at 10° C. Then, the polymer adsorbate is crosslinked at 80° C. and under reduced pressure of 50 mbar for 2 h. The polymer-coated ion exchanger was then cooled down to room temperature.

The particles are then transferred to suitable suction filters and washed with the following solvents (BV=bed volume): 3 BV 0.1 M NaOH, 3 BV deionized water, 3 BV 0.2 M HCl, 3 BV water, 6 BV 0.1 M NaOH, 6 BV deionized water. The product BacCap is obtained as a water-wet particle.

Example 2

3 l Lewatit S 8227 from Lanxess is washed with 15 l deionized water on a frit with the porosity 3. 2270 g moist ion exchanger is then weighed out into a VT 5 vacuum shovel dryer from Lödige. The ion exchanger is dried at a jacket temperature of 80° C. and a pressure of 30 mbar and a rotational speed of 57 rpm for 2 h. After the drying, 915 g dried ion exchanger is poured back into the VT 5 vacuum shovel dryer. The jacket temperature is adjusted to 4° C. and, when the product temperature lies below 20° C., within 15 minutes 600 ml deionized water is conveyed by means of a peristaltic pump into the mixer, which is operated at a rotational speed of 180 rpm. For the coating, 227 g polyvinylamine solution (polymer content 10%) batch: PC 18007 and 227 g deionized water are weighed out into a vessel. As crosslinker, 9.20 g ethylene glycol diglycidyl ether (EGDGE) [2224-15-9] is weighed out into another vessel. The crosslinker is added to the polymer solution and intensively mixed. The mixture is then conveyed into the Lödige mixer within 5 min using a peristaltic pump. The rotational speed of the mixer is adjusted to 240 rpm and the jacket temperature is left at 4° C. After the addition, mixing was continued for 15 min at 240 rpm. The jacket temperature on the dryer is then adjusted to 80° C. and the rotational speed is controlled down to 120 rpm.

Then, the particles are again cooled down to room temperature and are then transferred to suitable suction filters and washed with the following solvents: 3 BV 0.1 M NaOH, 3 BV deionized water, 3 BV 0.1 M HCl, 6 BV water. The product BacCap is obtained as a water-wet particle.

Example 3

500 g carrier material, sulfonated polystyrene PRC 15035 (average pore size 450 Å, average particle size 500 μm) with a water absorption capacity of 1.35 ml/g, is sucked directly into a VT5 ploughshare mixer from Lödige. The product temperature in the dryer is adjusted to 10° C. The mixer is operated at 180 revolutions per minute. Once the product temperature in the mixing drum has reached 10° C., 225 g non-desalinated polyvinylamine solution batch: PC 16012 (polymer content 12%) cooled to 10° C., 20 g ethylene glycol diglycidyl ether (EGDGE) CAS No. [2224-15-9] and 430 g deionized water are weighed out into a vessel. The mixture is placed in the mixer within 10 min and mixed for 1 h at 10° C. Then, the polymer adsorbate is crosslinked at 65° C. The product is then cooled down to room temperature. The particles are then transferred to suitable suction filters and washed with the following solvents: 3 BV 1 M NaOH, 3 BV deionized water, 3 BV 2 M HCl, 3 BV water, 6 BV 1 M NaOH, 6 BV deionized water. 1297 g product is obtained as a water-wet particle. Anion capacity (AIC): 471 μmol/g.

Example 4

Instructions for the preparation of a porous particle of a crosslinked polymer with a particle size of 100 μm (batch: BV 18007): 1st preparation of polymer adsorbate: 750 g carrier material, silica gel (AGC Si-Tech Co. M.S Gel D-200-100 batch: 164M00711), is conveyed directly into a VT5 ploughshare mixer from Lödige. The product temperature is adjusted to 10° C. The mixer is operated at 180 revolutions per minute. Once the product temperature in the mixing drum has reached 10° C., 1125 g non-desalinated polyvinylamine solution batch: PC 18007 (polymer content 10%), cooled to 10° C., is weighed out into a vessel and 23.2 g ethylene glycol diglycidyl ether (EGDGE) CAS No. [2224-15-9] is added. The mixture is placed in the mixer within 10 min and mixed for 1 h at 10° C. Then, the polymer adsorbate is dried at 80° C. and 50 mbar (approx. 2 h). The coated silica gel was then cooled down to 10° C. For the 2nd coating, 750 g polymer solution PC 18007 (polymer content 10%), cooled to 10° C., was weighed out into a vessel and 15 g ethylene glycol diglycidyl ether (EGDGE) CAS No. [2224-15-9] was added. The polymer solution was poured into the mixing drum within 5 min. The polymer adsorbate was mixed for 30 min at 10° C. Then, the temperature in the Lödige mixer was increased again to 65° C. for 1 h. 3 l deionized water was added to the polymer adsorbate. This suspension is used for the crosslinking. The coated silica gel suspended in water is transferred into a 10-l glass reactor with automatic temperature control. The suspension is stirred and heated to 80° C. Then, 317 g epichlorohydrin CAS No. [106-89-8] is added within 20 min, with the result that the temperature in the reactor does not exceed 85° C. 211 g 1,2-diaminoethane [107-15-3] is then added dropwise within 20 minutes. The second addition of 317 g epichlorohydrin CAS No. [106-89-8] is then effected within 20 minutes, followed by 211 g 1,2-diaminoethane CAS No. [107-15-3] again. At the end, 317 g epichlorohydrin CAS No. [106-89-8] is finally added and the reaction is stirred for 1 h at 85° C. The reaction mixture is then cooled to 25° C., and 1500 ml 50% NaOH is added and the reaction mixture is stirred for 12 hours. The template particles are then transferred to suitable suction filters and washed with the following solvents: 3 BV 1 M NaOH, 3 BV deionized water, 3 BV 2 M HCl, 3 BV water, 6 BV 1 M NaOH and 6 BV deionized water.

The product is obtained as a moist filter cake.

Example 5

An absorber resin, prepared according to Example 1, Example 3 or Example 4, is suspended in a solvent, e.g. DMF. Then, 110 mol % glycidyl-2,2,3,3,4,4,5,5-octafluoropentyl ether (based on the amino groups of the starting resin, FIG. 1) is added to the stirred suspension of the resin and the suspension is stirred for 12 h at 70° C. Then, the suspension is rinsed with a syringe with the following solvents: 3 BV DMF, 3 BV n-heptane, 3 BV 1 M HCl in DMF, 3 BV 1 M NaOH in DMF and 3 BV DMF. Again a 50% suspension in DMF is then prepared. In a second reaction step, 110 mol % glycidyl-2,2,3,3,4,4,5,5-octafluoropentyl ether is again added to this suspension. The reaction mixture is then stirred for 12 h at 70° C. Then, the absorber resin is rinsed with the following solvents: 3 BV DMF, 3 BV n-heptane, 3 BV 1 M HCl in DMF, 3 BV 1 M NaOH in DMF and 3 BV MeOH. The absorber resin can then be dried in vacuo to constant weight.

The structure of the absorber resin is shown in FIG. 2.

Example 6

The absorber resin as prepared in Example 5, activated charcoal (100 Å, 45 µm) and commercial C-18 chromatography gel (Kromasil, C18, 100 Å, 10 µm) are each poured into an HPLC column with the dimensions 33.5×4 mm, the column is sealed, and they are subjected to a frontal analysis. For this, a solution of 100 ppm perfluorooctanoic acid in water is prepared and pumped through the column until the capacity is exhausted. The breakthrough is measured by UV spectrometry at 205 nm.

The table below (Table 1) gives the absorber capacities for perfluorooctanoic acid measured on the three absorbers:

TABLE 1

Perfluorooctanoic acid capacity of the perfluorosurfactant-selective instrAction gel ND 150201 in comparison with commercial absorbers

| | Column | | |
|---|---|---|---|
| | PV 150778 | PV 150775 | PV 150772 |
| | | Resin Batch | |
| | EP 14433 | EP 15010 | ND 150201 |
| | | Perfluorooctanoic acid | |
| ME 15036 | Kromasil C18 | Activated Charcoal | modified instrAction resin |
| Up-Take [mg/ml phase] | 0 | 64 | 220 |

As Table 1 shows, the absorber capacity for perfluorooctanoic acid on the instrAction phase (batch no. ND 150201) is approx. 3-4× larger than on the activated charcoal. Commercial RP18 gel shows no absorption of perfluorooctanoic acid.

The breakthrough curve of the frontal analysis is shown in FIG. 3.

Example 7

A suspension of the instrAction resin (BV 18009, prepared as in Example 3) in water is prepared and poured into the cartridge with axial throughflow such that a bed volume of approx. 100 ml results (bed dimensions: approx. 6.3×9 cm on average).

Then, a suspension of E. coli ($10^4$-$10^5$ CFU/l) with a flow rate of 100-500 ml/min (60-300 BV/h) per hour, increasing in stages, is pumped through the cartridge. The effluent is collected after approx. 3-5 min at each flow rate stage and then investigated for remaining bacteria using standard processes.

The result of the investigations is shown in FIG. 5: over the entire investigation range no bacteria can be detected in the effluent. This means that the bacteria are removed completely, in a concentration relevant to drinking water.

Example 8

An instrAction resin as prepared in Example 3 is investigated for activity against P. aeruginosa as follows: 500 g of the resin washed with tap water is incubated in a reaction vessel with a suspension of $10^6$ CFU Pseudomonas aeruginosa in 10 ml tap water. After 3, 6, 12 and 24 hours samples are taken and investigated for Pseudomonas aeruginosa using standard processes. The result is shown in FIG. 6: after only three hours of incubation bacteria can no longer be detected.

Example 9

Water Filter Jugs

Water filter jugs customary in the trade from Brita and BWT were filled with mixtures of instrAction resins according to the invention, prepared according to Example 1 or 2 and Example 3, with activated charcoal in the ratio 1:1 and compared with the original cartridges with added silver, comparing for bacteria growth.

For this, firstly 1 l of a suspension of 8.3×$10^5$ cfu/l E. coli was added to the cartridges, which were stored and investigated for eluting bacteria after 3 weeks.

The result of the investigations can be seen in FIG. 7.

As expected, no bacteria can be detected in the rinsing media of the original cartridges with added silver from BWT and Brita since the added silver in the cartridges is partially eluted and accordingly prevents bacterial growth in the filtrate. The cartridges with the mixtures of the resins claimed here and activated charcoal, likewise no bacteria or only a number of bacteria that is strongly reduced to close to the detection limit compared with the input quantities can be detected.

The bacteriostatic effect of the resins claimed in the present application is thus demonstrated. The undesired added silver in the cartridges is thus superfluous.

The filtration speed, which is important for the application, of the cartridges filled with mixtures of the resins claimed here and activated charcoal is in the same range in comparison with the commercial cartridges with added silver.

BRIEF DESCRIPTION OF THE DRAWINGS

List of Figures

Figure 1:
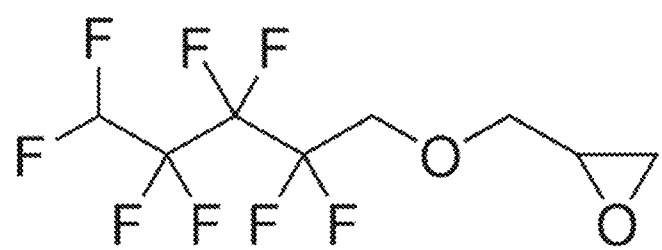
FIG. 1: Glycidyl 2,2,3,3,4,4,5,5-octafluoropentyl ether.
Figure 2:
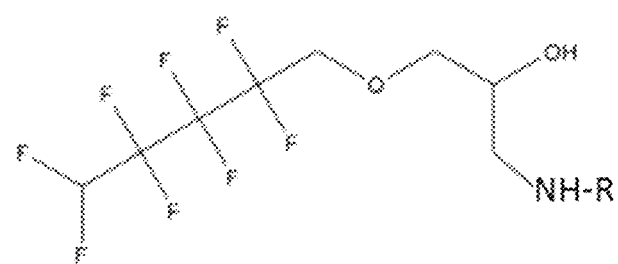
FIG. 2: One of two structural isomers of the absorber for perfluorinated surfactants (R=polymer).
Figure 3:
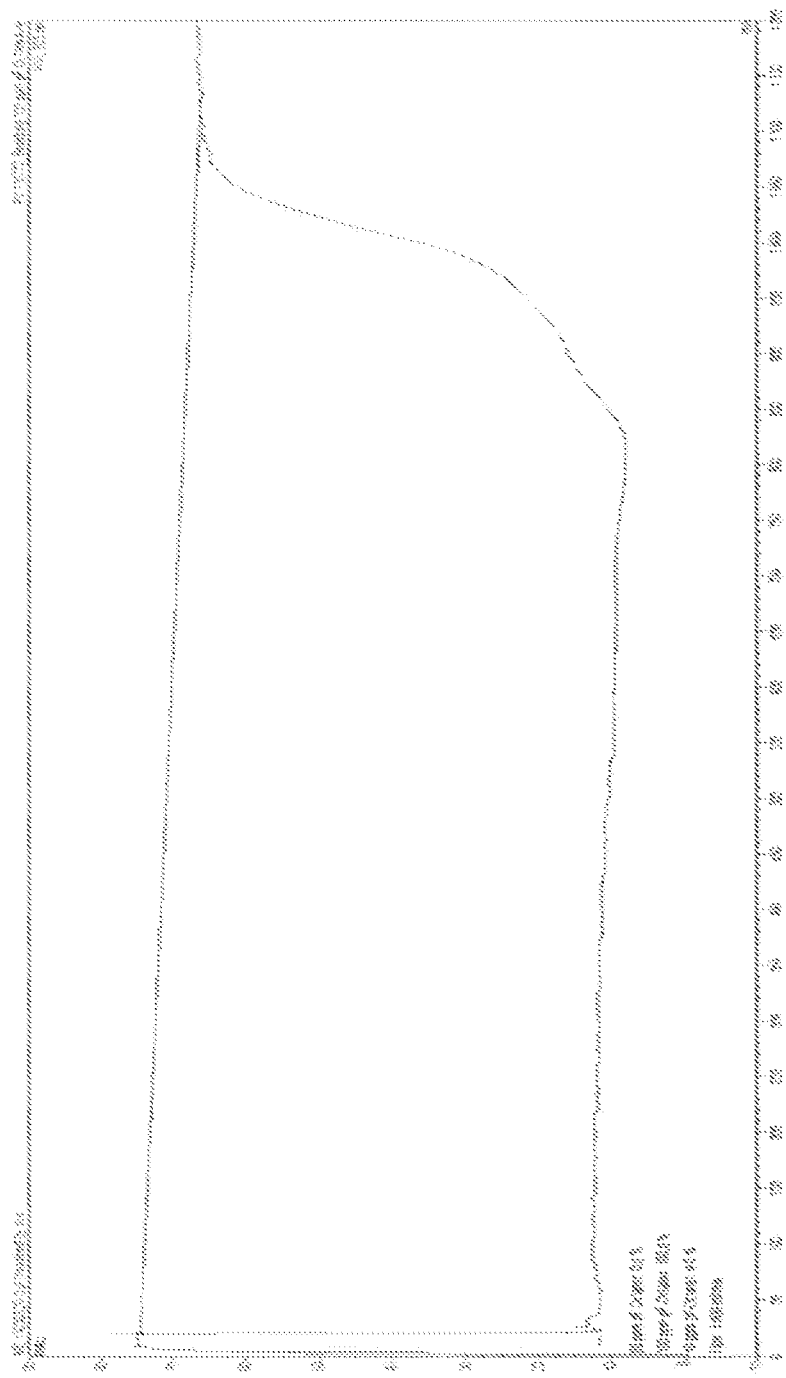
FIG. 3: Chromatographic breakthrough profile on PV 150772 (instrAction resin batch: batch no. ND 150201); the breakthrough is not achieved until after approx. 900 min or 220 mg perfluorooctanoic acid per ml resin.
Figure 4:
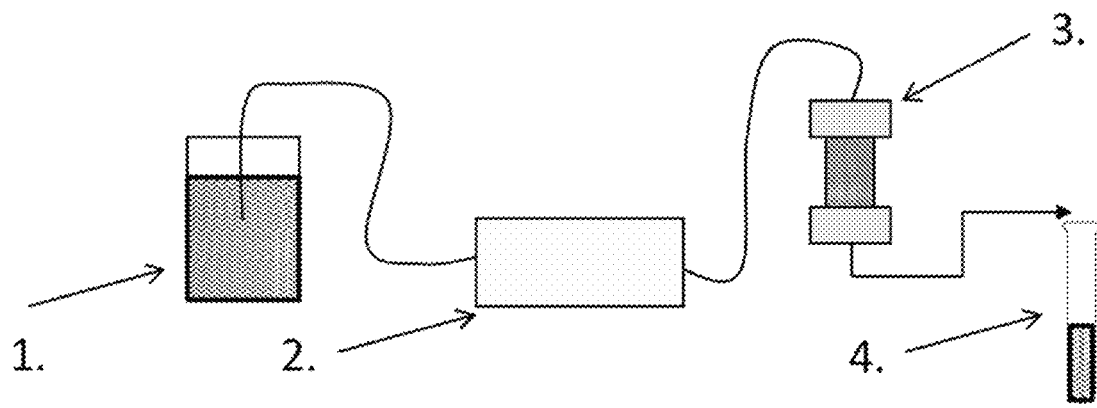
FIG. 4: Experimental set-up for investigating the bacterial depletion by BacCap resin; 1. storage vessel with bacteria suspension, E. coli, $10^4$ Cfu/l, 2. pump, 3. column/cartridge with instrAction BacCap resin, 4. faction).
Figure 5:
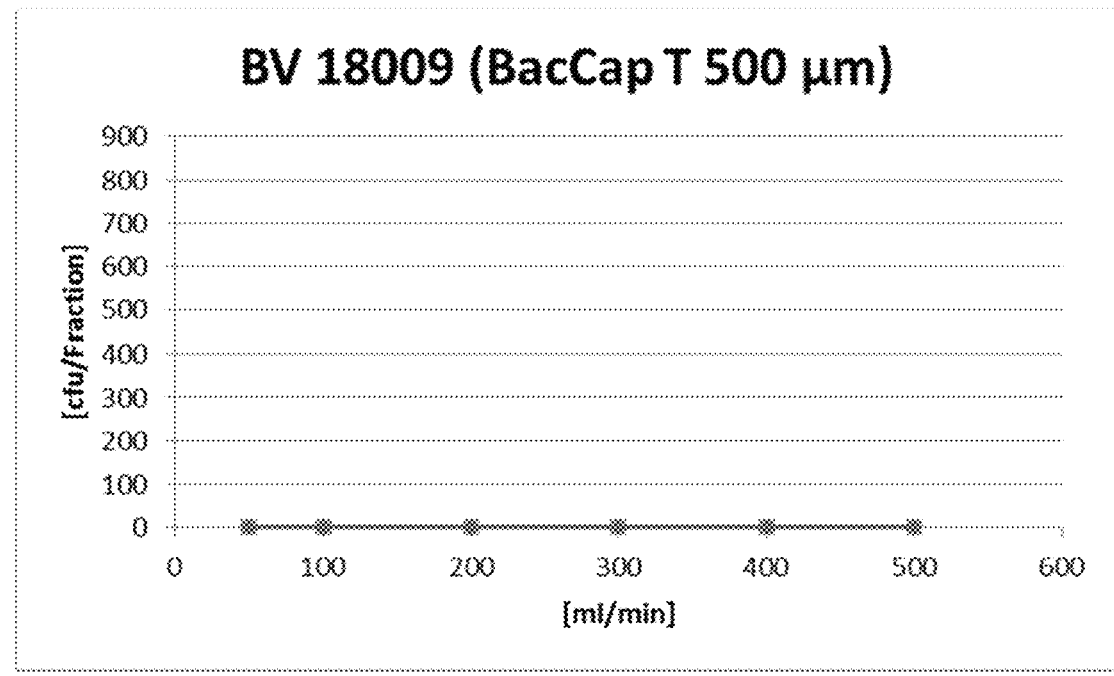
FIG. 5: Result of the dynamic bacteria removal on the ion exchanger only coated externally.
Figure 6:
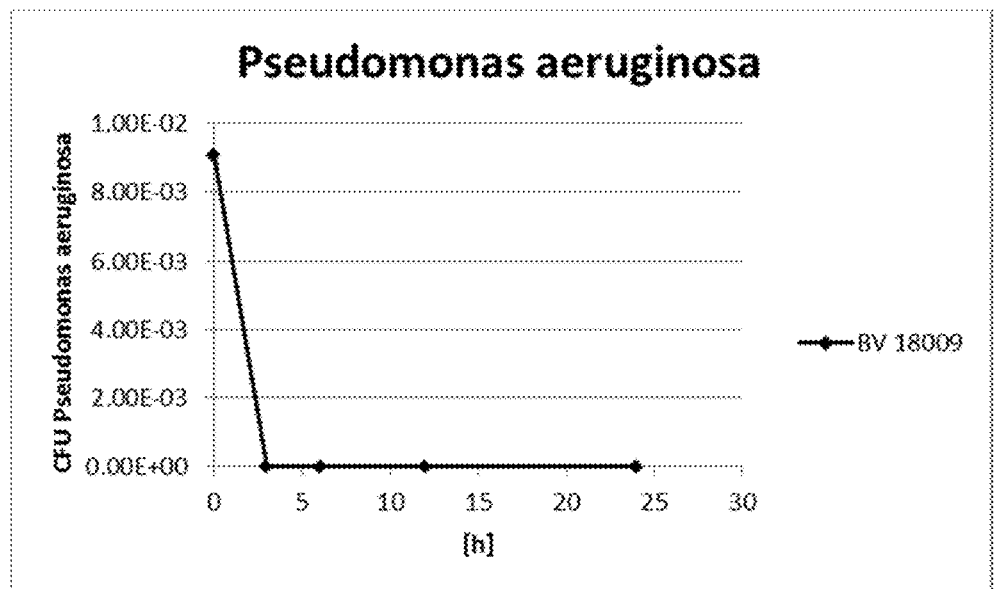
FIG. 6: Concentration progression over time of Pseudomonas aeruginosa in the presence of instrAction BacCap resin under static conditions.
Figure 7:
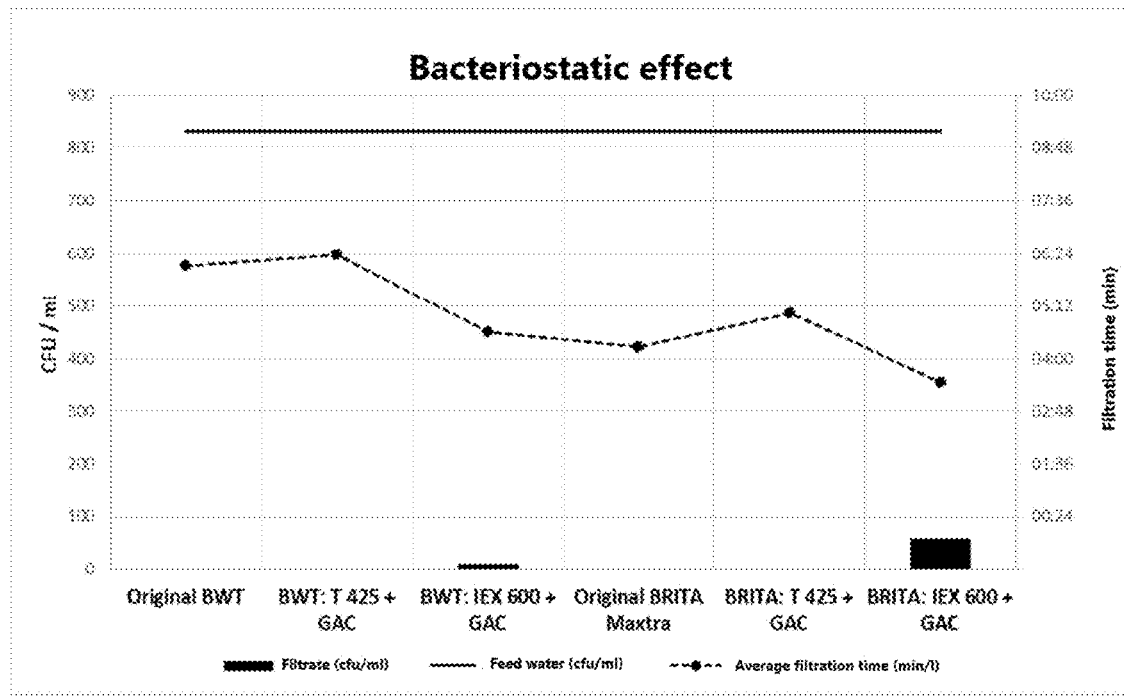
FIG. 7: Bacteriostatic effect.

The invention claimed is:
1. Process for preparing porous particles with an antibacterial coating, wherein the process comprises:
(a) providing an aqueous suspension containing a polyamine, a crosslinker, and a porous organic carrier material in particle form at a temperature lower than or equal to 10° C. in a mixer;

(b) coating, in the mixer, the organic carrier material with the polyamine only on an outer surface of the carrier material; and
(c) crosslinking the polyamine only on the outer surface of the porous organic carrier material and simultaneously removing water;
wherein pores of the porous organic carrier material have a size ranging from 20 nm to 100 nm, and the polyamine has a size of 10,000-20,000 g/mol.

2. Process according to claim 1, wherein a), b) and c) are repeated at least once.

3. Process according to claim 1, wherein the crosslinking is effected in a stirred reactor.

4. Process according to claim 1, wherein the polyamine is used in a non-desalinated state.

5. Process according to claim 1, wherein the porous organic carrier material is a polystyrene.

6. Process according to claim 1, wherein the porous organic carrier material is a strong or a weak anion exchanger.

7. Process according to claim 1, wherein the porous organic carrier material is selected from polystyrene, polymethacrylate and polyacrylate.

8. Process according to claim 1, wherein the polyamine is a polyvinylamine.

9. Porous particles prepared by the process according to claim 1.

10. Process for removal of bacteria from water or other aqueous solutions comprising contacting the water or aqueous solutions with the porous particles according to claim 9.

11. Process for removal of heavy metals from water or other aqueous solutions comprising contacting the water or aqueous solutions with the porous particles according to claim 9.

12. Process for removal of anions of elementic acids and anions of elementous acids comprising contacting the anions of elementic acids and the anions of elementous acids with the porous particles according to claim 9.

* * * * *